United States Patent [19]

Hilditch

[11] 4,193,993
[45] Mar. 18, 1980

[54] COMPOSITIONS CONTAINING PRESERVATIVE METALS AND THEIR USE FOR THE PRESERVATION OF WOOD AND LIKE MATERIALS AND AS FUNGICIDES

[75] Inventor: Edward A. Hilditch, Somerset, England

[73] Assignee: Cuprinol Limited, Somerset, England

[21] Appl. No.: 904,606

[22] Filed: May 10, 1978

[30] Foreign Application Priority Data

May 12, 1977 [GB] United Kingdom ............... 20089/77

[51] Int. Cl.$^2$ ........................ A01N 13/00; A01N 9/00
[52] U.S. Cl. .................................... 424/141; 424/145; 424/166; 424/287; 424/289; 424/294; 424/295
[58] Field of Search ............... 424/166, 140, 145, 141, 424/287, 289, 295, 294

[56] References Cited

U.S. PATENT DOCUMENTS

| | | | |
|---|---|---|---|
| 4,001,400 | 1/1977 | Hager | 424/166 |
| 4,020,180 | 4/1977 | Woerner | 424/166 |

OTHER PUBLICATIONS

Chemical Abstracts, vol. 84 (1976), p. 26867x.
Chemical Abstracts, vol. 77 (1972), p. 166469z.
Chemical Abstracts, vol. 77 (1972), p. 128290b.

*Primary Examiner*—V. D. Turner
*Attorney, Agent, or Firm*—Sprung, Felfe, Horn, Lynch & Kramer

[57] ABSTRACT

Compositions in the form of an aqueous solution comprising:
 (a) a compound of a preservative metal;
 (b) a branched-chain carboxylic acid or a dipentene-mono-carboxylic acid or a dipentene-di-carboxylic acid; and
 (c) ammonia and/or an ammonium compound, the amount of ammonia and/or ammonium compound being at least sufficient to solubilize the compound (a) and to neutralize the acid (b), are useful for the preservation of wood and like materials by impregnation into or surface application to the material and are also useful as fungicides for the treatment of plants for agricultural and horticultural use.

58 Claims, No Drawings

COMPOSITIONS CONTAINING PRESERVATIVE METALS AND THEIR USE FOR THE PRESERVATION OF WOOD AND LIKE MATERIALS AND AS FUNGICIDES

BACKGROUND OF THE INVENTION

The present invention relates to a composition in the form of an aqueous solution of a compound of a preservative metal and certain organic acids solubilized by means of ammonia or an ammonium compound. The invention also relates to the use of such a composition for the preservation of porous materials, particularly porous fibrous materials, such as wood, textiles, ropes, cordage and leather. The invention relates still further to the use of these compositions as agricultural of horticultural fungicides.

The value of compounds of cobalt, iron, manganese, nickel and, more particularly, copper and zinc (hereinafter collectively referred to as "preservative metals") as wood preservatives has been known for a long time. The use of such compounds, particularly of copper, as agricultural and horticultural fungicides is also known. In order to apply the copper or other metal compound to wood in a manner suitable for it to act as a wood preservative, it is necessary first to dissolve the compound in a carrier liquid which is capable of penetrating into the wood. It is further necessary, if the resulting wood-preserving effect is to last for an acceptable length of time, that, after treatment and evaporation of the carrier liquid, together with any initial "curing" or fixation period, the metal compound impregnated into the wood should not be able readily to be leached out by the action of water. Many ways of achieving this have been suggested. For example, it has been proposed to use a water-insoluble metal compound which is soluble in an organic solvent, so that, after evaporation of the organic solvent used as carrier, the water-insoluble metal compound remains in the wood. Examples of such compounds are the copper salts of naphthenic acid or of the organic acids produced by the Koch or Oxo processes, such as 2-ethylhexoic acid, 3,3,5-trimethylnonanoic acid or mixtures of such acids available under various trade names, for example Acid 810, Versatic 10 and the Cekanoic acids.

These acids themselves possess some fungicidal and/or insecticidal properties and, although this is much less than that of copper and the other preservative metals, because they are usually present in an amount by weight several times greater than that of the metal, these acids may add usefully to the efficiency of the combination, particularly in cases where there are present fungal species which can tolerate relatively large amounts of copper or other metal. The acid and metal are normally present in a stoichiometric ratio; however, an excess of acid may be present or, where a basic metal compound can be formed, as with zinc, there may be less than one equivalent of acid for each equivalent of metal. Compositions of this type based upon copper naphthenate have been available for commercial use for about 60 years and are the subject of many national standards, such as British Standards 3770 and 5056. Similar materials based on the branched-chain carboxylic acids, such as the 2-ethylhexoic and 3,3,5-trimethylnonanoic acids referred to above, although a more recent development, have also been in commercial use for several years.

Because these materials are used in solution in organic solvent carriers (such as white spirit, paraffin or related aliphatic or aromatic solvents), they penetrate very readily into the wood or other porous material, but, in certain situations, the requirements for effective protection of the timber or other material necessitate impregnation of fluid throughout the whole of the material. Processes achieving this use large volumes of carrier liquid which, because of the cost of such liquids, make the process uneconomic and also can give rise to a fire or health hazard.

These preservative metals, particularly copper, and these acids also have some fungicidal effect when applied to plants and, as when compositions comprising metal and acid are used for the preservation of timber, it is necessary, when treating plants, that the composition should be applied in the form of a solution but that, once applied, the preservative composition should resist leaching by water. However, organic solvents can represent a very serious fire and health hazard when applied freely to plants and, in some cases, may cause damage to the plants. Furthermore, for domestic use, where the compositions may not be stored under ideal conditions and may be mishandled, organic solvents should, where possible, be avoided.

Water is an inexpensive carrier liquid and an alternative way of depositing compounds of copper or other metals in wood in such a manner that they will resist leaching out by water is to prepare a solution of the compound in water in such a manner that, after impregnation into the wood or application to the plant, a chemical change occurs whereby the formerly soluble metal compound is deposited in an insoluble form. One such method involves dissolving the copper or other metal compound in a solution of ammonia or of an ammonium salt, such as ammonium carbonate or bicarbonate, so that, after treatment, the ammonia evaporates, leaving the copper compound in the required water-insoluble form. United Kingdom Patent Specification No. 599,443, for example, describes the solubilization by such methods of copper and zinc salts of naphthenic acids and their derivatives, saturated and unsaturated carboxylic acids containing more than 10 carbon atoms and abietic acid, and their use for the preservation of textile materials. United Kingdom Patent Specification No. 1,379,095 describes the use of "normal", i.e. straight-chain, fatty acids containing from 6 to 11 carbon atoms per molecule (generally caprylic acid) solubilized in this manner for wood preservation and discloses that carboxylic acids containing more than 11 or less than 6 carbon atoms are unsatisfactory, for one reason or another, as wood preservatives.

BRIEF SUMMARY OF THE INVENTION

It is an object of the present invention to provide a composition suitable for use as a wood preservative or as an agricultural or horticultural fungicide in the form of an aqueous solution containing a compound of a preservative metal and a branched-chain carboxylic acid or a dipentene-mono-carboxylic acid or a dipentene-di-carboxylic acid solubilized by means of ammonia and/or an ammonium compound.

It is a further object of the invention to provide a process for the treatment of a porous organic material, particularly wood, by applying to the material the aqueous solution of the invention.

It is a still further object of the invention to provide a process for the protection of plants from fungal attack by applying to the plant the aqueous solution of the invention.

We have surprisingly found that certain metallic compounds of branched-chain carboxylic acids, particularly aliphatic carboxylic acids, such as those which may be produced by the Koch and Oxo processes, and metallic compounds of the mono- and di-carboxylic acid derivatives of dipentene, when solubilized by means of ammonia can be used in an aqueous medium for the impregnation of wood and of other organic fibrous products.

Thus, the present invention consists in an aqueous solution comprising:

(a) a compound of a preservative metal preferably selected from the group consisting of copper, zinc, cobalt, iron, manganese and nickel;

(b) an organic acid selected from the group consisting of branched-chain carboxylic acids, dipentene-mono-carboxylic acids and dipentene-di-carboxylic acids; and (c) an ammoniacal compound selected from the group consisting of ammonia, ammonium compounds and mixtures thereof, the amount of ammoniacal compound being at least sufficient to solubilize said compound (a) and to neutralize said organic acid (b).

This aqueous solution can be used for the preservation of porous organic materials, such as wood, by applying it to such materials by such methods as impregnation, coating etc. The solution is also useful as an agricultural or horticultural fungicide by application to the plants to be treated.

DETAILED DESCRIPTION OF INVENTION

The preservative metal in compound (a) is preferably copper, zinc, cobalt, iron, manganese or nickel, more preferably copper, zinc or cobalt and most preferably copper. The compound itself is preferably insoluble in water but soluble in an aqueous ammoniacal solution. Examples of such compounds are cuprous oxide, copper carbonate, copper hydroxide (copper hydrate), cupric oxide, basic cupric acetate, copper arsenate, copper arsenite, copper acetoarsenite (Paris Green), the naturally occurring basic copper carbonate ores (such as malachite and blue azurite), zinc arsenate, zinc carbonate, zinc oxide, cobalt arsenate and cobalt hydroxide (cobalt hydrate). Copper metal can also be used as a source of copper, provided that a suitable solubilizing agent, for example air, is present to ensure that sufficient copper has dissolved. We prefer cuprous oxide, copper carbonate or copper hydroxide. The materials used need not be pure chemicals but can be industrial grade materials containing a greater or lesser percentage of the preservative metal than the formula amount.

The second component (b) of the composition is an organic acid. Where the organic acid is a branched-chain carboxylic acid, it is preferably an aliphatic acid and preferably has from 6 to 20, more preferably from 7 to 13 and most preferably from 8 to 10, carbon atoms in its molecule; it may have one or more aromatic substituents. A single such acid or a mixture of two or more such acids may be employed and it is possible to use either the pure acid or a commercially available product. Mixtures of isomers of octanoic, nonanoic and other acids are commercially available as "iso-octanoic acid", "iso-nonanoic acid" etc. and mixtures of isomers of acids with different numbers of carbon atoms in the molecule are available under such trade names as Acid 810 (AKZO), Versatic 10 (Shell) and Cekanoic acid (Ugine Kuhlmann).

Alternatively, or in addition to the branched-chain carboxylic acids, it is possible to use mono- and di-carboxylic acids derived from dipentene. Such acids are described by Von Boy Cornils and Rita Payes in Chemiker Zeitung, Sonderdruck 98 (1974) pages 70–76. Examples include the mono-acids of formula

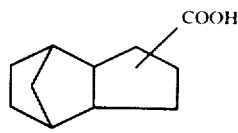

e.g. tricyclo[5.2.1.0$^{2,6}$]decan-3(4)-carboxylic acid and the di-acids of formula

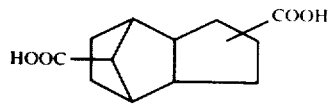

A mixture of tricyclo[5.2.1.0$^{2,6}$]decan-3-carboxylic acid and tricyclo[5.2.1.0$^{2,6}$]decan-4-carboxylic acid is available under the trade name TCD acid S and mixtures of the di-acids are available under the trade name TCD acid DS, both from Ruhrchemie AG.

We have found that the organic acids used in the aqueous solution of the present invention has, when used in such solution, the advantage of superior antifungal activity over previously used types of acid, for example the straight-chain $C_6$ to $C_{11}$ acids. Although we do not wish to be bound by any theory, it is believed that the molecular configuration of the organic acids used in the present invention permits more ready penetration into the cells in wood and similar materials.

The proportion of organic acid to preservative metal may be that required by simple stoichiometry, i.e. one equivalent of metal per equivalent of acid, in which case, on evaporation of the ammonia, a simple salt of the metal and the acid will be deposited. It will, therefore, be appreciated that, in place of using a separate acid and preservative metal compound in the aqueous solution of the invention, the acid and a metal compound may first have been reacted, to produce a preservative metal salt of the acid and this salt may be added, as such, to the aqueous solution; in such a case, the amount of ammoniacal compound added must be such that it solubilizes the preservative metal-organic acid compound previously prepared.

The amount of acid may be less than the stoichiometric proportion, in which case the compound deposited may be a basic salt or a mixture of a simple salt of the acid and a totally inorganic salt, such as a carbonate or basic carbonate or mixture thereof. The use of a ratio of acid to metal such that only part of the deposited compound is in the form of a salt of the organic acid and part is in the form of an inorganic salt may be particularly advantageous economically. In such a case, the amount of acid may be reduced to any desired level, provided that sufficient is retained to show the desired anti-fungal effect. The acid may also be present in an amount greater than the stoichiometric proportion.

The third essential component of the aqueous solution is a water-soluble ammoniacal compound. This compound may be an ammonium salt, preferably ammonium carbonate or ammonium bicarbonate, or ammonia itself or a mixture of such a salt and ammonia, most preferably a mixture of ammonium carbonate and ammonia. The amount of ammonia present, either as ammonia itself or in the form of an ammonium salt, should be at least sufficient fully to complex the metal. For example, when the preservative metal is copper, the minimum molar ratio of ammonia to copper in order fully to complex the copper is 4:1. For most purposes, it is preferred that the ammonia should be present in some excess. When both ammonium carbonate and ammonia are used, the ratio of ammonium carbonate to ammonia and the total excess of each should be chosen having regard to the eventual use of the solution. For example, in a solution containing 4 moles of ammonium carbonate per gram atom of copper and having a high concentration of copper, only a small amount of ammonia need be added to produce a stable solution; however, if the concentration of copper in the solution is low, a much larger excess must be used. The amount of ammonia must also be at least sufficient fully to neutralize the carboxylic acid present in order to ensure solubilization of the acid.

The solution is preferably prepared by mixing the copper or other preservative metal compound with an aqueous solution of the ammonia and/or ammonium compound. The carboxylic acid may be added to the ammoniacal solution of the metal compound at any stage during its preparation; alternatively, a separate solution may be prepared, first adding sufficient ammonia solution, preferably diluted for safety reasons to the organic acid to neutralize it, and then mixing this solution with the solution of preservative metal compound. As a further alternative, where a salt of the preservative metal and the organic acid is used ab initio, the salt, the ammonia and/or the ammonium compound and water can be mixed together in a single operation. Preparation of the solution is preferably carried out at ambient temperature, although it proceeds quite satisfactorily at sub-ambient temperatures, which have the advantage that loss of ammonia is reduced. If heat is applied, care must be taken to avoid an excessive evaporation of ammonia.

An alternative method of preparation is to dissolve an inorganic compound of the preservative metal in an aqueous solution of ammonia and to pass carbon dioxide through this solution. The carboxylic acid component is then added in either of the ways already described.

Other materials known to be of value as wood preservatives (for example, compounds of arsenic and/or boron), wax emulsions, resin emulsions and colouring compounds may be added to these solutions for use in any situation where their additional properties may be of value. Furthermore, aqueous solutions according to the present invention may advantageously be mixed with acrylic resin emulsions, styrene-acrylic resin emulsions, polyvinyl acetate emulsions, natural latex or similar emulsions and, in particular, with such emulsions having a fine particle size as are described in West German patent specification No. 2,531,895. The resulting composition can be used as a combined preservative and finish to retain the natural appearance of the timber or other material to which the resulting composition is to be applied.

The invention thus further consists in a process for the treatment of a porous organic material by applying to the material the aqueous solution of the invention or a composition containing said aqueous solution.

Application of the solution to the porous organic material may be by any method used with conventional solutions of this type, for example long or short steeping, spraying, methods involving application of vacuum and/or pressure or simple contact of the solution with the surface of the material to be treated. Treatment is preferably effected by a pressure technique, for example of the types known as "Bethell", "Lowry" or "Reuping"; the solution may also be applied by simple soaking of the timber in the solution for a sufficiently long period of time; these methods are most commonly used for the treatment of seasoned timber. Solutions may equally be used to treat unseasoned timber by diffusion for example by the "Boucherie process" or by any other of the well-known techniques for allowing preservatives to diffuse into wet wood. The solution may also be thickened to a paste by means of suitable additives to provide a composition which can be applied as a paste in situ to the outside of poles, railway sleepers and other timbers already in service, to provide additional preservation. Where the aqueous solution is mixed, as described above, with an emulsion to provide a combined preservative and finish, the resulting composition is preferably applied to the surface of timber by brushing or spraying.

Although the solutions of the present invention are of particular value in the treatment of solid timber and, for this reason, the treatment of solid timber has been described in detail above, they may also, by adoption of suitable application techniques, be used for the treatment of wood chips or other fibrous materials, including paper pulp, textiles, ropes, cordage and leather and means for treating these materials are well-known to those skilled in the art.

The aqueous solutions of the present invention, particularly those containing copper as the preservative metal, are also valuable for the treatment of seeds or growing plants in agriculture, horticulture or home garden use to prevent the growth and spread of fungal disease. The solutions may be applied by any method used for the application of known fungicidal solutions, but are most preferably applied by spraying. The solutions of the invention have the same or better preventative effect against fungal disease than known compositions and have better resistance to washing off, thus remaining active at the site of application for a longer period.

The invention is further illustrated by the following Examples, in which percentages are by weight.

EXAMPLE 1

120 g of powdered copper hydroxide and 200 g of ammonium carbonate were dissolved in a mixture of 200 g of aqueous ammonia (specific gravity 0.88) and 758 g of water. The resulting solution is hereinafter referred to as "Component 1".

Meanwhile, 248 g of the commercially available tertiary carboxylic acid known under the Trade Mark Versatic 10 were dissolved in a mixture of 220 g of aqueous ammonia (specifc gravity 0.88) and 423 g of water to give a solution hereinafter referred to as "Component 2".

To prepare a concentrated solution, 50 ml of Component 1 were mixed with 40 ml of Component 2. The mixture was a clear blue solution which remained stable over a period of 3 months. This concentrated solution contained 3.40 copper and was used as such in the biological tests described in Example 30.

When the concentrated solution was diluted with 10 times its volume of water, a precipitate formed but it was found that the addition of a further small quantity of ammonia served to stabilize the solution. Accordingly, a dilute solution was prepared by mixing 50 ml of the concentrated solution, 40 ml of aqueous ammonia (specific gravity 0.88) and 500 ml of water and this solution remained stable for over 3 months.

EXAMPLE 2

The procedure described in Example 1 was repeated, except that Component 2 was replaced by Component 3, a solution comprising 108 g of Acid 810 (AKZO), 110 g of aqueous ammonia (specific gravity 0.88) and 282 g of water. Both concentrated and dilute solutions prepared according to the procedure of Example 1 were clear blue, stable solutions.

EXAMPLES 3 to 8

The procedure described in Example 1 was repeated, except that Component 2 was replaced by solutions having the compositions shown in the following Table 1.

Table 1

| Example No. | Acid Amount (g) | Type | Aqueous Ammonia (SG 0.88) Amount (g) | Water Amount (g) |
| --- | --- | --- | --- | --- |
| 3 | 104 | Iso-octanoic | 110 | 286 |
| 4 | 113 | Iso-nonanoic | 110 | 277 |
| 5 | 151 | Iso-tridecanoic | 111 | 239 |
| 6 | 103 | Cekanoic C8 | 145 | 287 |
| 7 | 113 | Cekanoic C9 | 110 | 277 |
| 8 | 123 | Cekanoic C10 | 110 | 267 |

"Cekanoic" is a Trade Mark for a series of branched-chain carboxylic acids available from Ugine Kuhlmann and the abbreviation "SG" stands for "specific gravity".

All were stable solutions and both concentrated and dilute solutions were also stable.

EXAMPLE 9

88.4 g of cuprous oxide were mixed with 200 g of ammonium carbonate and 200 g of aqueous ammonia (specific gravity 0.88); 789.6 g of water were added to form a clear solution.

80 ml of the resulting solution were added to 100 ml of Component 3, prepared as described in Example 2. A clear, stable, concentrated solution was formed. On mixing 50 ml of this concentrated solution with 40 ml of aqueous ammonia (specific gravity 0.88) and 500 ml of water, a more dilute solution which was also stable was formed.

EXAMPLES 10-19

A solution, Component A, containing the preservative metal compound was prepared by mixing a preservative metal compound, ammonium bicarbonate and/or ammonium carbonate, ammonia solution of specific gravity 0.88 and water at ambient temperature in the proportions shown in Table 2, in which all parts and percentages are by weight.

Table 2

| Example No. | Metal Compound Compound | Metal Compound Amount (parts) | Ammonium bicarbonate (parts) | Ammonium carbonate (parts) | Ammonia solution SG 0.88 (parts) | Water (parts) |
| --- | --- | --- | --- | --- | --- | --- |
| 10 | Copper Carbonate (53% Cu) | 56.6 | — | 38.8 | 78.4 | 370.2 |
| 11 | Copper Carbonate (53% Cu) | 56.6 | 38.8 | — | 74.0 | 405.1 |
| 12 | Copper Hydrate (62.5% Cu) | 48.0 | 102.1 | 69.0 | 105.2 | 219.7 |
| 13 | Copper Hydrate (62.5% Cu) | 48.0 | 102.1 | 69.0 | 105.2 | 219.7 |
| 14 | Nickel Hydroxide (59.5% Ni) | 50.4 | — | 212.1 | 188.1 | 249.4 |
| 15 | Nickel Hydroxide (59.5% Ni) | 50.4 | — | 212.1 | 188.1 | 249.4 |
| 16 | Zinc Oxide (80% Zn) | 37.5 | 52.1 | 7.6 | 50.7 | 365.6 |
| 17 | Basic Zinc Carbonate (57.5% Zn) | 52.2 | 29.8 | 80.5 | 88.0 | 249.5 |
| 18 | Cobalt Hydrate (61% Co) | 49.2 | 97.8 | 235.0 | 132.0 | 163.6 |
| 19 | Cobalt Hydrate (61% Co) | 49.2 | 18.6 | 37.7 | 244.6 | 283.7 |

Meanwhile a Component B was prepared by mixing together an organic acid, ammonia solution of specific gravity 0.88 and water in the proportions shown in Table 3, in which all parts are by weight.

Table 3

| Example No. | Organic Acid Acid | Organic Acid Amount (parts) | Ammonia solution SG 0.88 (parts) | Water (parts) |
| --- | --- | --- | --- | --- |
| 10 | Isotridecanoic | 150 | 55.9 | 294.1 |
| 11 | Cekanoic C10 | 150 | 169.4 | 180.6 |
| 12 | Acid 810 | 150 | 145.5 | 204.5 |
| 13 | Acid 810 | 150 | 145.5 | 204.5 |
| 14 | Versatic 10 | 150 | 84.0 | 260.0 |
| 15 | Versatic 10 | 150 | 84.0 | 260.0 |
| 16 | Versatic 10 | 150 | 336.0 | 14.0 |
| 17 | Isotridecanoic | 150 | 179.2 | 170.8 |
| 18 | Isotridecanoic | 150 | 179.2 | 170.8 |
| 19 | Cekanoic C8 | 150 | 302.5 | 47.5 |

Components A and B were then mixed together at ambient temperature in the proportions by weight shown in Table 4.

Table 4

| Example No. | Component A | Component B |
| --- | --- | --- |
| 10 | 106 | 35.2 |
| 11 | 84 | 139.0 |
| 12 | 106 | 258.0 |
| 13 | 105.9 | 50.3 |
| 14 | 136.9 | 57.8 |
| 15 | 68.5 | 130.3 |
| 16 | 55.2 | 121.4 |
| 17 | 54.4 | 123.5 |
| 18 | 66.6 | 211.7 |
| 19 | 62.2 | 146.6 |

All solutions were stable and could be diluted with water to produce dilute solutions which themselves were stable.

Preparation of two separate ammoniacal solutions as done in these Examples is not, however, essential and other procedures which may be adopted are illustrated by the following Examples.

EXAMPLE 20

3.97 g of zinc oxide were mixed with 5.25 g of ammonium bicarbonate, 0.8 g of ammonium carbonate, 5.37 g of aqueous ammonia of specific gravity 0.88 and 38.7 g of water, and the whole was stirred at ambient temperature until completely dissolved. A further 77.8 g of aqueous ammonia of specific gravity 0.88 were added, followed by 34.7 g of Versatic 10, which dissolved to give a clear, stable solution dilutable with water.

EXAMPLE 21

56.6 g of copper carbonate were mixed with 50 g of isotridecanoic acid to form a paste; to this were added 38.8 g of ammonium carbonate and 141 g of aqueous ammonia of specific gravity 0.88. This was then thoroughly mixed to give a thick paste, which could be diluted with water to produce a stable solution.

EXAMPLE 22

To 204 g of zinc versatate (previously prepared) were added 54.8 g of ammonium carbonate, 81 g of ammonium bicarbonate, 264 g of aqueous ammonia solution of specific gravity 0.88 and 150 g of water. This was thoroughly mixed at ambient temperature until a single phase solution was obtained. On addition of further water to give a mixture of total weight 1,000 g, a clear, stable solution was obtained.

EXAMPLE 23

25 g of the copper salt of the mixture of tricyclo-[5.2.1.0$^{2,6}$]decan-3(4)-carboxylic acids sold under the trade name TCD acid S were mixed with 30.6 g of aqueous ammonia of specific gravity 0.88, 17.3 g of ammonium carbonate and 51 g of water. This gave a homogeneous, thick paste which, on addition of 200 g of water, yielded a clear, stable solution which could be further diluted with water to produce a dilute solution which, itself, was stable.

EXAMPLE 24

A solution of 40 g of ammonium bicarbonate in a mixture of 100 ml of water and 80 g of aqueous ammonia of specific gravity 0.88 was prepared by mixing at ambient temperature. To this solution were added 13 g of copper hydroxide (57.3% by weight Cu) and 20 g of zinc oxide. Mixing was continued until a clear solution was obtained, at which point 55 g of Versatic 10 acid were added. This dissolved to give a clear, stable solution which could be further diluted with water.

EXAMPLE 25

12 g of Versatic 10 acid were mixed with 12 g of Acid 810. This mixture was then added to a solution of 80 g of aqueous ammonia of specific gravity 0.88 and 100 g of water. When the acid had dissolved, 40 g of ammonium bicarbonate were added, followed by 50 g of aqueous ammonia, forming a cloudy suspension. To this were added 18.5 g of copper hydroxide (57.3% Cu) and 5 g of zinc oxide. Mixing was continued at ambient temperature until a clear solution was obtained. This solution could be further diluted with water to give a dilute solution which itself was stable.

EXAMPLE 26

By way of comparison, the present Example illustrates a composition of the type described in the prior art. Specifically, it uses a straight-chain fatty acid of the type disclosed in United Kingdom patent specification No. 1,379,095.

120 g of copper hydroxide were mixed at ambient temperature with 200 g of ammonium carbonate, 200 g of aqueous ammonia of specific gravity 0.88 and 758 g of water until thoroughly dissolved. Meanwhile, a separate solution was prepared by dissolving 206 g of caprylic acid in 220 g of aqueous ammonia of specific gravity 0.88 and 423 g of water. 500 ml of the copper-containing solution were then mixed with 400 ml of the caprylic acid-containing solution to produce a fungicidal solution. The concentrated fungicidal solution thus obtained contains 3.40% copper, and was used for the biological tests described in Example 30.

EXAMPLE 27

100 ml of Component 1, prepared as described in Example 1, were mixed with 25 ml of Component 3, prepared as described in Example 2, to give a concentrated solution containing 4.892% copper. This solution was used for the biological tests described in Example 30.

EXAMPLE 28

A concentrated solution was prepared by mixing:
cuprous oxide: 10.78 kg
ammonium bicarbonate: 50.00 kg
Acid 810: 4.98 kg
aqueous ammonia (specific gravity 0.88): 34.34 kg.

The product contained 9.5% copper and could be diluted with water. Dilute solutions containing 3.2%, 4.8% and 6.4% of this concentrated solution were used to treat timber by a conventional full cell pressure treatment process to a liquid retention of approximately 300 kg per cubic meter. The timber thus treated was found to be resistant to fungal attack.

These solutions, and also more concentrated ones containing 9.6 and 12.8% by weight of the concentrated solution, were also used to treat timber by a conventional empty cell pressure process to a liquid retention of approximately 150 kg per cubic meter. Again, the treated timber was found to be resistant to fungal attack.

EXAMPLE 29

A concentrated solution was prepared by mixing:
cuprous oxide: 10.78 kg
ammonium bicarbonate: 50.00 kg
Acid 810: 40.00 kg
aqueous ammonia (specific gravity 0.88): 49.76 kg.

The resulting concentrated solution contained 6.3% copper and could be diluted with water.

Dilute solutions containing 3.2%, 4.8%, 6.4% and 9.6% of this concentrated solution were used to treat wood by a full cell pressure process to a liquid retention of approxmately 300 kg per cubic meter. The treated wood was found to be resistant to fungal attack.

EXAMPLE 30

The biological effectiveness of compositions according to the present invention, as well as the prior art composition described in Example 26, was demonstrated by the following test.

Small blocks of wood (*Pinus sylvestris* sapwood) of dimensions 3.0×1.0×0.5 cm were impregnated with the preservative solution prescribed in the following Table 5 using the vacuum technique prescribed by British Standard 838. After drying, each wood block was placed into contact with the mycellium of *Coniophora* cerebella growing on a malt-agar medium containing 3% malt, 1.5% agar and 0.5% peptone. After incubation for 6 weeks, the blocks were removed and the change in weight was determined. This weight change gave an indication of the extent to which the fungus had been able to attack the wood—the greater the weight loss, the greater the extent of attack and thus the less effective the preservative.

Table 5

| Preservative Solution | Preservative Loading in Test Block Kg/m³ | | Weight Loss % |
|---|---|---|---|
| | "Concentrated" Solution | Copper (Cu) | |
| Concentrated Solution according to Example 1 | 29.6 | 1.00 | 6.67 |
| | 26.0 | 0.88 | 6.93 |
| | 14.0 | 0.48 | 6.37 |
| | 14.5 | 0.50 | 6.63 |
| Concentrated Solution according to Example 27 | 32.7 | 1.60 | 7.13 |
| | 31.6 | 1.56 | 7.39 |
| | 15.2 | 0.74 | 6.20 |
| | 15.8 | 0.77 | 6.33 |
| | 17.1 | 0.84 | 6.70 |
| | 15.3 | 0.75 | 6.65 |
| Concentrated Solution according to Example 26 | 14.8 | 0.50 | 14.28 |
| | 14.1 | 0.48 | 7.58 |
| Copper-Chrome-Arsenate | (3.08)* | | 5.70 |
| Salts to BS4072 Type 2 | (2.94)* | | 6.36 |
| Untreated | 0 | 0 | 63.50 |
| | 0 | 0 | 53.79 |

*Total dry salts

It can be seen that the weight loss when employing the concentrated solution of the present invention is reproducibly low, whereas higher weight losses are obtained when using the prior art solution of Example 26.

EXAMPLE 31

26 g of the zinc salt of tricyclo[5.2.1.0$^{2,6}$]decan-3(4), 8(9)-dicarboxylic acid (TCD acid DS) were mixed with 34.5 g of ammonium carbonate and 20.3 g of aqueous ammonia (specific gravity 0.88) to form a thin paste, which gave a clear solution upon the addition of 250 g of water.

On further dilution of 50 g of this solution with 200 g of water, a clear, stable, dilute solution was obtained, which could be used as described above for the impregnation and treatment of wood and other porous materials to provide an effective fungicidal effect.

I claim:

1. In an aqueous ammoniacal preservative composition comprising: p1 (a) a composition of a preservative metal selected from the group consisting of copper, zinc, cobalt, iron, manganese and nickel;
   (b) an organic acid; and
   (c) an ammoniacal compound selected from the group consisting of ammonia, ammonia compounds, and mixtures thereof, the amount of ammoniacal compound being at least sufficient to solubilize said compound (a) and to neutralize said acid (b), the improvement wherein said organic acid is a branched chain carboxylic acid having 6 to 20 carbon atoms, a dipentene monocarboxylic acid, a dipentene dicarboxylic acid, or a mixture thereof present in a preserving amount.

2. The composition of claim 1, wherein the organic acid is a branched-chain carboxylic acid.

3. The composition of claim 2, wherein the branched-chain carboxylic acid is an aliphatic acid having from 7 to 13 carbon atoms.

4. The composition of claim 3, wherein the acid is selected from the group consisting of the isomers of octanoic and nonanoic acids and mixtures thereof.

5. The composition of claim 1, wherein the dipentene mono- carboxylic acid is a mixture of tricyclo[5.2.1.0$^{2,6}$]-decan-3(4)-carboxylic acids.

6. The composition of claim 1, wherein the organic acid is a mixture of dipentene di-carboxylic acids.

7. The composition of claim 1, wherein the ammoniacal compound is ammonia.

8. The composition of claim 1, wherein the ammoniacal compound is an ammonium salt.

9. The composition of claim 1, wherein the ammoniacal compound is selected from the group consisting of ammonium carbonate and ammonium bicarbonate.

10. The composition of claim 1, wherein the ammoniacal compound is a mixture of ammonia and an ammonium salt selected from the group consisting of ammonium carbonate and ammonium bicarbonate.

11. The composition of claim 1, wherein the preservative metal is copper.

12. The composition of claim 1, wherein the preservative metal is zinc.

13. The composition of claim 1, which additionally contains an emulsion selected from the group consisting of acrylic resin emulsions, styrene-acrylic resin emulsions, polyvinyl acetate resin emulsions and natural latex.

14. In an aqueous ammoniacal preservative composition comprising:
   (a) a composition of a preservative metal selected from the group consisting of copper, zinc, cobalt, iron, manganese and nickel;
   (b) an organic acid; and
   (c) an ammoniacal compound selected from the group consisting of ammonia, ammonia compounds and mixtures thereof, the amount of ammoniacal compound being at least sufficient to solubilize said compound (a).

the improvement wherein said organic acid is a branched chain carboxylic acid having 6 to 20 carbon atoms, a dipentene monocarboxylic acid, a dipentene dicarboxylic acid or a mixture thereof present in a preserving amount.

15. The composition of claim 14, wherein the organic acid is a branched-chain carboxylic acid.

16. The composition of claim 15, wherein the branched-chain carboxylic acid is an aliphatic acid having from 7 to 13 carbon atoms.

17. The composition of claim 16, wherein the acid is selected from the group consisting of the isomers of octanoic and nonanoic acids and mixtures thereof.

18. The composition of claim 14, wherein the dipentene mono-carboxylic acid is a mixture of tricyclo[5.2.1.0$^{2,6}$]-decan-3(4)-carboxylic acids.

19. The composition of claim 14, wherein the organic acid is a mixture of dipentene di-carboxylic acids.

20. The composition of claim 14, wherein the ammoniacal compound is ammonia.

21. The composition of claim 14, wherein the ammoniacal compound is an ammonium salt.

22. The composition of claim 14, wherein the ammoniacal compound is selected from the group consisting of ammonium carbonate and ammonium bicarbonate.

23. The composition of claim 14, wherein the ammoniacal compound is a mixture of ammonia and an ammonium salt selected from the group consisting of ammonium carbonate and ammonium bicarbonate.

24. The composition of claim 14, wherein said preservative metal is copper.

25. The composition of claim 14, wherein said preservative metal is zinc.

26. A composition as claimed in claim 14, additionally comprising an emulsion selected from the group consisting of acrylic resin emulsions, styrene-acrylic resin emulsions, polyvinyl acetate resin emulsions and natural latex.

27. A composition according to claim 1 wherein said organic acid is a dipentene mono-carboxylic acid or dipentene di-carboxylic acid of the formulae

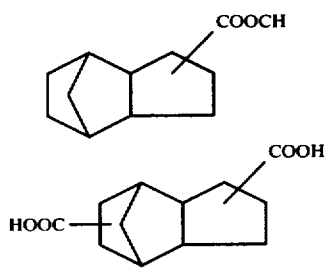

28. A composition according to claim 1 wherein said ammoniacal compound is ammonia, ammonium carbonate, ammonium bicarbonate or a mixture of ammonia with ammonium carbonate.

29. A process for the treatment of a porous organic material which comprises applying to said material an aqueous ammoniacal preservative of claim 1 in a preserving amount.

30. A process as claimed in claim 29, wherein the organic acid is a branched-chain carboxylic acid.

31. A process as claimed in claim 30, wherein the branched-chain carboxylic acid is an aliphatic acid having from 7 to 13 carbon atoms.

32. A process as claimed in claim 31, wherein the acid is selected from the group consisting of the isomers of octanoic and nonanoic acids and mixtures thereof.

33. A process as claimed in claim 29, wherein the dipentene mono-carboxylic acid is a mixture of tricyclo[5.2.1.0$^{2,6}$]decan-3(4)-carboxylic acids.

34. A process as claimed in claim 29, wherein the organic acid is a mixture of dipentene di-carboxylic acids.

35. A process as claimed in claim 29, wherein the ammoniacal compound is ammonia.

36. A process as claimed in claim 29, wherein the ammoniacal compound is an ammonium salt.

37. A process as claimed in claim 29, wherein the ammoniacal compound is selected from the group consisting of ammonium carbonate and ammonium bicarbonate.

38. A process as claimed in claim 29, wherein the ammoniacal compound is a mixture of ammonia and an ammonium salt selected from the group consisting of ammonium carbonate and ammonium bicarbonate.

39. A process as claimed in claim 29, wherein the preservative metal is copper.

40. A process as claimed in claim 29, wherein the preservative metal is zinc.

41. A process as claimed in claim 29, wherein the composition additionally contains an emulsion selected from acrylic resin emulsions, styrene-acrylic resin emulsions, polyvinyl acetate resin emulsions and natural latex.

42. A process as claimed in claim 29, wherein the compound (a) and the acid (b) are reacted together in a preliminary step to produce a compound of said preservative metal with said organic acid.

43. A process as claimed in claim 29, wherein the aqueous solution is applied by long or short steeping.

44. A process as claimed in claim 43, wherein pressure is applied during the steeping period.

45. A process as claimed in claim 29, wherein the aqueous solution is applied to unseasoned timber by a diffusion process.

46. A process as claimed in claim 29, wherein the aqueous solution is applied to the surface of a porous organic material in the form of a paste.

47. A process for protecting seeds and growing plants against fungal attack which comprises applying to the seeds and the growing plants an aqueous solution comprising:
(a) a compound of copper;
(b) an organic acid selected from the group consisting of branched-chain carboxylic acids, dipentene mono-carboxylic acids, dipentene di-carboxylic acids and mixtures thereof; and
(c) an ammoniacal compound selected from the group consisting of ammonia, ammonium compounds and mixtures thereof, the amount of ammoniacal compound being sufficient to solubilize said compound (a) and to neutralize said acid (b).

48. A process as claimed in claim 47, wherein the organic acid is a branched-chain carboxylic acid.

49. A process as claimed in claim 48, wherein the branched-chain carboxylic acid is an aliphatic acid having from 7 to 13 carbon atoms.

50. A process as claimed in claim 47, wherein the acid is selected from the group consisting of the isomers of octanoic and nonanoic acids and mixtures thereof.

51. A process as claimed in claim 47, wherein the dipentene mono-carboxylic acid is a mixture of tricyclo[5.2.1.0$^{2,6}$]decan-3(4)-carboxylic acids.

52. A process as claimed in claim 47, wherein the organic acid is a mixture of dipentene di-carboxylic acids.

53. A process as claimed in claim 47, wherein the ammoniacal compound is ammonia.

54. A process as claimed in claim 47, wherein the ammoniacal compound is an ammonium salt.

55. A process as claimed in claim 47, wherein the ammoniacal compound is selected from the group consisting of ammonium carbonate and ammonium bicarbonate.

56. A process as claimed in claim 47, wherein the ammoniacal compound is a mixture of ammonia and an ammonium salt selected from the group consisting of ammonium carbonate and ammonium bicarbonate.

57. A process as claimed in claim 47, wherein the compound (a) and the acid (b) are reacted together in a preliminary step to produce a compound of said preservative metal with said acid.

58. A process as claimed in claim 47, wherein, prior to application, the aqueous solution is mixed with an emulsion selected from the group consisting of acrylic resin emulsions, styrene-acrylic resin emulsions, polyvinyl acetate resin emulsions and natural latex.

* * * * *